Table I -continued

| Organisms | | BB-K 186 "3'-deoxy-butirosin A" | MIC (mcg/ml) Bu-1975C₁ "4'-deoxy-butirosin A" | Bu-1709A₁ "butirosin A" |
|---|---|---|---|---|
| K. pneumoniae | D11 | 0.8 | 0.8 | 0.8 |
| " | 22-3038 | 3.1 | 6.3 | >100 |
| Ent. cloacae | A20364 | 1.6 | 3.1 | 1.6 |
| " | A21006 | 3.1 | 6.3 | >100 |
| Pr. vulgaris | A9436 | 0.4 | 0.8 | 0.4 |
| Pr. morganii | A20031 | 3.1 | 3.1 | 1.6 |
| Pr. mirabilis | A9554 | 1.6 | 1.6 | 1.6 |
| Prov. stuartii | A20894 | 25 | >100 | >100 |
| Ps. aeruginosa | A9930 | 0.8 | 1.6 | 6.3 |
| " | A20635 | 25 | >100 | >100 |
| " | No. 130 | 12.5 | 25 | 25 |
| " | A20601 | 12.5 | 25 | 50 |
| " | A20896 | 50 | 50 | >100 |
| " | GN-315 | >100 | >100 | >100 |
| Pseudomonas sp. | A20621 | 100 | >100 | 100 |
| Ser. marcescens | A20019 | 6.3 | 6.3 | 6.3 |
| " | A21247 | 3.1 | 6.3 | 6.3 |
| S. aureus | Smith | 0.8 | 1.6 | 0.8 |
| " | D193 | 1.6 | 3.1 | 3.1 |
| " | D133 | 3.1 | 6.3 | 6.3 |
| " | D137 | 12.5 | 25 | 25 |
| " | A20239 | 3.1 | 6.3 | 25 |

The above data show that compound 11 (BB-K186) is equal to or superior in most respects to butirosin A and 4'-deoxybutirosin A in its activity against a variety of diseases organisms. It is particularly improved in its activity against Pseudomonas aeruginosa. In most instances, it is 2 to 4 fold as active as butirosin A, and in some instances 8 to 30 times as active.

Compound 11 is valuable as an antibacterial agent, nutritional supplement in animal feeds, therapeutic agent in poultry and animals, including man, and are especially valuable in the treatment of infectious diseases caused by Gram-positive and Gram-negative bacteria.

Compounds 11 when administered orally is useful as an adjunctive treatment for preoperative sterilization of the bowel. Both aerobic and anaerobic flora which are suseptible to this drug is reduced in the large intestine. When accompanied by adequate mechanical cleansing, it is useful in preparing for colonic surgery.

The novel medicament provided by the present invention may be formulated as pharamceutical compositions comprising, in addition to the active ingredient, a pharmaceutically acceptable carrier or diluent. The compound may be administered both orally and parenterally. The pharmaceutical preparation may be in solid form such as capsules, tablets, or dragees, or in liquid form such as solutions, suspensions or emulsions. In the treatment of bacterial infections in man, the compound of this invention may be administered parenterally in an effective amount of from about 250 mg. to about 3000 mg. per day in divided doses three or four times a day. Generally the compound is effective when administered at a dosage of about 5.0 to 7.5 mg./kg. of body weight every 12 hours. Thus, it is administered in man in dosage units containing, e.g. 125, 250 or 500 mg. of active ingredient with suitable physiologically acceptable carriers or excipients.

DESCRIPTION OF THE PREFERRED EMBODIMENTS

EXAMPLE 1

Tetra-N-benzyloxycarbonylbutirosin A (2)*

Figure 1:
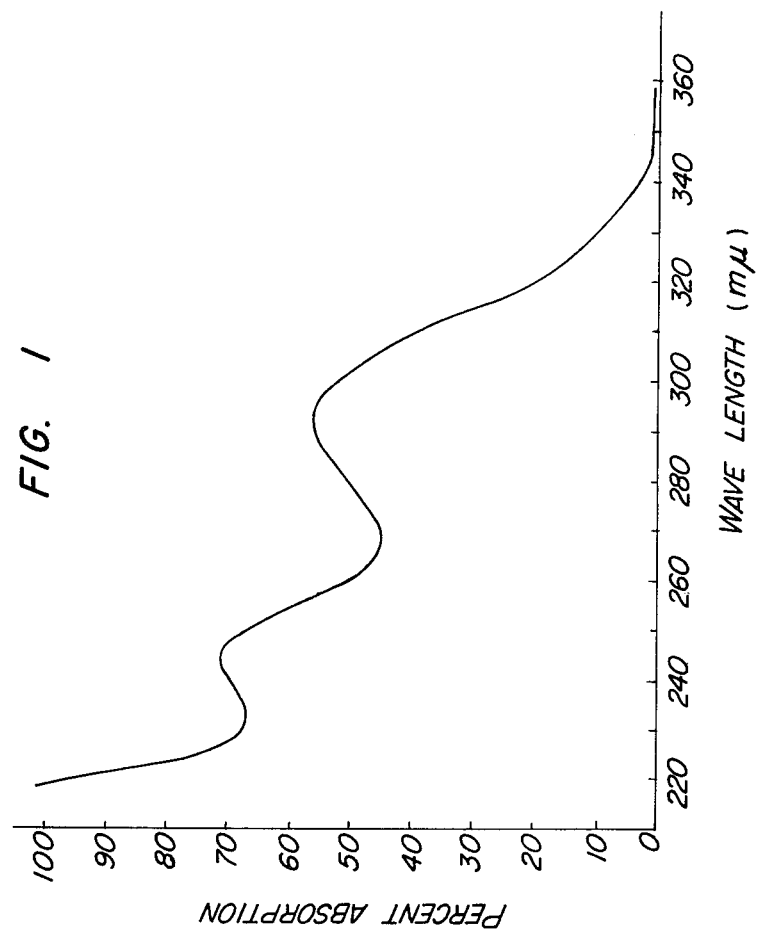

To a stirred mixture of 19.5 g. (35 mmoles) of butirosin A (1) and 8.20 g. (77.3 mmoles) of $Na_2CO_3$ in 440 ml. of 20% aqueous acetone was added dropwise 26.2 g. (153 mmoles) of benzyl chloroformate under cooling. The reaction mixture was stirred overnight at room temperature to give an oily precipitate, which was separated from the supernatant by decantation, washed thoroughly with water and triturated with ether to give 34.23 g. (89%) of 2.

*T. B. Culbertson, D. R. Watoson and T. H. Haskell, J. Antibiot. 26, 790 (1973).

EXAMPLE 2

Tetra-N-benzyloxycarbonyl-3',4';3'',5''-di-O-isopropylidenebutirosin A (4)

A solution of 14.3 g. (13.1 mmoles) of 2, 30 ml. of 2,2-dimethoxypropane and 60 mg. of p-toluenesulfonic acid in 250 ml. of DMF (dimethylformamide) was allowed to stand at room temperature for 2 days, then evaporated in vacuo to remove the MeOH formed. The concentrate was treated with another 10 ml. of 2,2-dimethoxypropane, kept at 60°C. for 2 hours, treated with about 1 ml. of $Et_3N$ and evaporated to dryness in vacuo. The oily residue was chromatographed on a silica gel column (180 g.) and eluted with $CHCl_3$-MeOH to give 5.5 g. (36%) of the diacetonide 4 and 8.45 g. (57%) of the monoacetonide 3*. Repeated isopropylidenation of 3 gave additional amount of 4. Total yield of 4 was 11.0 g. (72%). Monoacetonide (3), m.p. 123°–125°C.:

* Structure of 3 (monoacetonide)

METHOD FOR PREPARING 3-(METHYLMERCAPTO) PROPYLAMINOBLEOMYCIN

CROSS-REFERENCE TO THE RELATED APPLICATION

This application is a continuation-in-part of U.S. Ser. No. 177,332 filed on Sept. 2, 1971 now abandoned.

This invention relates to a method for preparing 3-(methylmercapto)propylaminobleomycin (hereinafter referred to as "demethylbleomycin $A_2$"). More particularly, it relates to a method for preparing demethylbleomycin $A_2$, which is characterized by thermally decomposing 3-(S,S-dimethylmercapto)propylaminobleomycin (hereinafter referred to as "bleomycin $A_2$").

Demethylbleomycin $A_2$ and bleomycin $A_2$ are represented by the following structural formula as metal free:

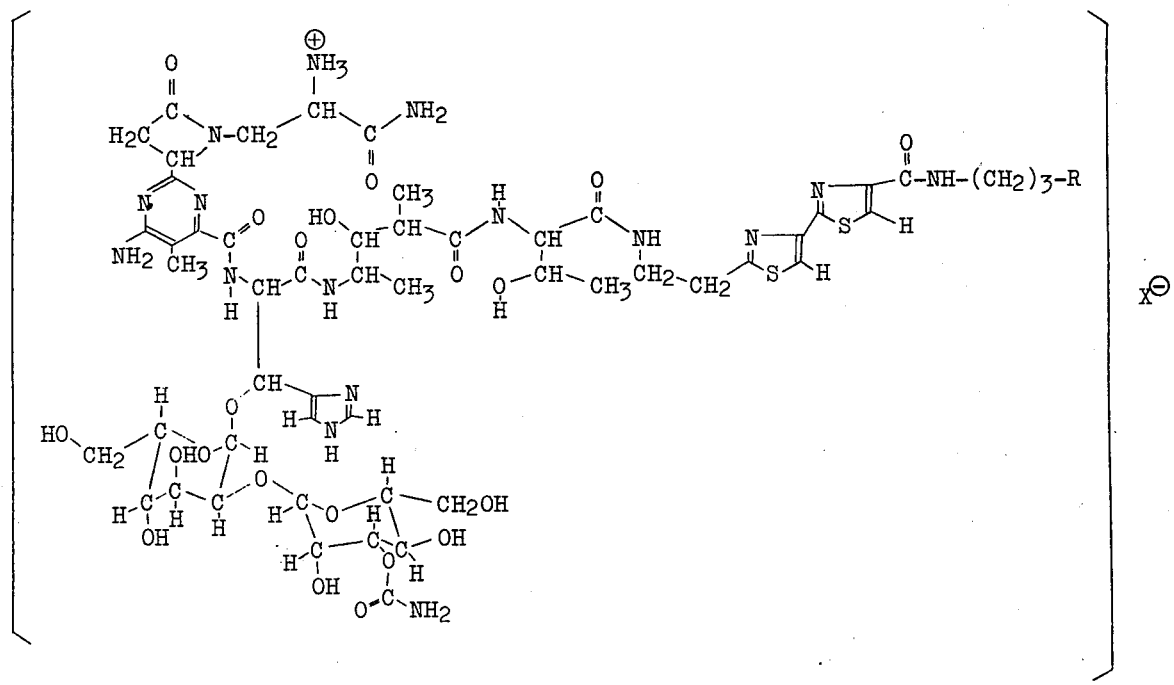

wherein
R = —S—CH$_3$ (in case of demethylbleomycin $A_2$) or

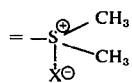

(in case of bleomycin $A_2$) and
X = Cl, Br, SO$_4$, H$_2$NSO$_3$,

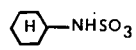

or CH$_3$COO.

These bleomycins are usually obtained in the state where a metal, e.g., copper, is contained in a chelete form, but their antimicrobial and carcinostatic activity are displayed by the part represented by the above formula. Accordingly, no metal is shown in the above formula.

Demethylbleomycin $A_2$ and bleomycin $A_2$ in this invention are meant to embrace both "metal-containing" and "metal-free" forms.

The bleomycins, which are carcinostatic antibiotics, are obtained by culturing bleomycin-producing strains of Actinomycetes *Streptomyces verticillus* in a nutrient medium (see Japanese Pat. No. 465,525 and U.S. Pat. No. 3,681,491).

By adding as a precursor an amino compound having both of a basic group and a primary amino group, there may selectively be obtained a known or novel bleomycin containing said amino compound as a side chain (see Belgian Pat. No. 745,926).

The present inventors had anticipated that a bleomycin having a 3-(methylmercapto)propylamino group as a side chain might be a useful substance and tried, in accordance with the said Belgian Patent, culturing with 3-(methylmercapto)propylamine used as a precursor, to obtain only a very small amount of the contemplated demethylbleomycin $A_2$.

This seemed to be resulted from poor assimilability of 3-(methylmercapto)propylamine into the bleomycin $A_2$ molecule as a side chain during culture, owing to absence of a basic group other than a primary amino group in 3-(methylmercapto)propylamine.

The present inventors thence made an extensive study on the preparation of demethylbleomycin $A_2$ and had a chance of thermally decomposing bleomycin $A_2$, the principal constituent of commerically produced bleomycin, to find out unexpectedly that bleomycin $A_2$ is easily demethylated into demethylbleomycin $A_2$ which was the objective substance of said study.

Based on said finding, the present invention has been accomplished.

In the present invention, may be used bleomycin $A_2$ (copper-containing hydrochloride) as formed in the culture medium. Any other bleomycin $A_2$ having any type of anion can be used since the type of anion of bleomycin $A_2$ has substantially no influence upon demethylation.

Bleomycin $A_2$ freed from copper by hydrogen sulfide or the like may be used as the starting material in this invention, though with the disadvantage of increased by-products of thermal decomposition.

The preparation of demethylbleomycin $A_2$ by demethylating bleomycin $A_2$ according to this invention can be carried out simply by heating bleomycin $A_2$ at about 80° to 140°C under ordinary pressure for 3 to 24 hours. Decomposition at unnecessarily high temperatures is unpreferable because of the decrease in yield due to side reactions. The heating may be carried out in the presence of non-solvents for bleomycin $A_2$ such as, for example, toluene, xylene, benzene, tetralin, cyclohexane, ethyl acetate, butyl acetate, and the like, added as a heating medium, whereas it is preferable to avoid the use of solvents for bleomycin $A_2$ such as water, methanol or the like because demethylation of bleomycin $A_2$ is greatly deterred in the presence of such solvents. The demethylation of bleomycin $A_2$ may be carried out under the condition of either increased pressure or reduced pressure. Especially, thermal decomposition under reduced pressure is advantageous in reducing the unfavorable oxidation induced by the atmospheric oxygen. The thermal decomposition under reduced pressure can be carried out by heating at 80° to 140°C under a reduced pressure of 200 mmHg, particularly under a reduced pressure of 15 to 50 mmHg, for 3 to 24 hours, and the after-treatment subsequent to the decomposition can be conducted in the same manner as in the case of the decomposition under ordinary pressure.

The decomposition products from the demethylating decomposition contain, beside demethylbleomycin $A_2$, undecomposed starting material, i.e., bleomycin $A_2$. To separate such a mixture into each component substance, the mixture is dissolved in an aqueous solution of ammonium chloride, and the solution is passed through a column packed with CM-Sephadex C-25 (trademark for a dry insoluble powder composed of microscopic beads which are synthetic organic compounds derived from the polysaccharide dextran, manufactured and sold by Pharmacia Fine Chemicals, Inc.), which had been treated with an aqueous solution of ammonium chloride. The mixture once adsorbed on the adsorbent is eluted with an aqueous solution of ammonium chloride, to obtain a blue solution of the objective demethylbleomycin $A_2$ of the present invention as the first fraction. On further elution with an aqueous ammonium chloride solution, the elute becomes colorless and then again turns blue. The blue elute containing undecomposed bleomycin $A_2$ is collected. The collected solutions of demethylbleomycin $A_2$ and bleomycin $A_2$ are treated in known ways. For example, the solution is passed through a column packed with an activated carbon for use in chromatography, Amberlite XAD-2 (trademark for an adsorbent resin manufactured and sold by Rohm and Haas Co.) or Amberlite CG-50 H-form (trademark for an ion exchange resin manufactured and sold by Rohm and Haas Co.) to allow demethylbleomycin $A_2$ or bleomycin $A_2$ to be adsorbed, then the column is washed with water, if necessary, furthermore with dilute acetic acid and water, to remove inorganic salts, and finally water miscible aqueous solvent containing dilute acid, for example a mixed solution of acetone, methanol or ethanol and dilute hydrochloric acid or dilute sulfuric acid, is passed through the column to collect a solution containing demethylbleomycin $A_2$ and a solution containing bleomycin $A_2$. The collected solution is admixed with a basic anion-exchange resin and pH is adjusted to 6.0. On removal of the solvent by distillation, each of the objective demethylbleomycin $A_2$ and undecomposed bleomycin $A_2$ can be obtained as a blue powder. Demethylbleomycin $A_2$ shows the following properties:

Demethylbleomycin $A_2$ (copper-containing hydrochloride) is a blue powder, decomposing slowly at 201° to 212°C. While soluble in water and methanol, it is insoluble in ethanol, propanol, butanol, ethyl acetate, ether, acetone, petroleum ether, benzene, and toluene.

| Elementary analysis ($C_{54}H_{79}N_{16}O_{21}S_3ClCu$) | | |
|---|---|---|
|  | Calculated | Found |
| C %, | 43.72 | 43.35 |
| H %, | 5.37 | 5.78 |
| N %, | 15.11 | 15.40 |
| O %, | 22.65 | 22.54 |
| S %, | 6.49 | 5.98 |
| Cl %, | 2.39 | 2.35 |
| Cu %, | 4.28 | 4.52 |

Figure 2:
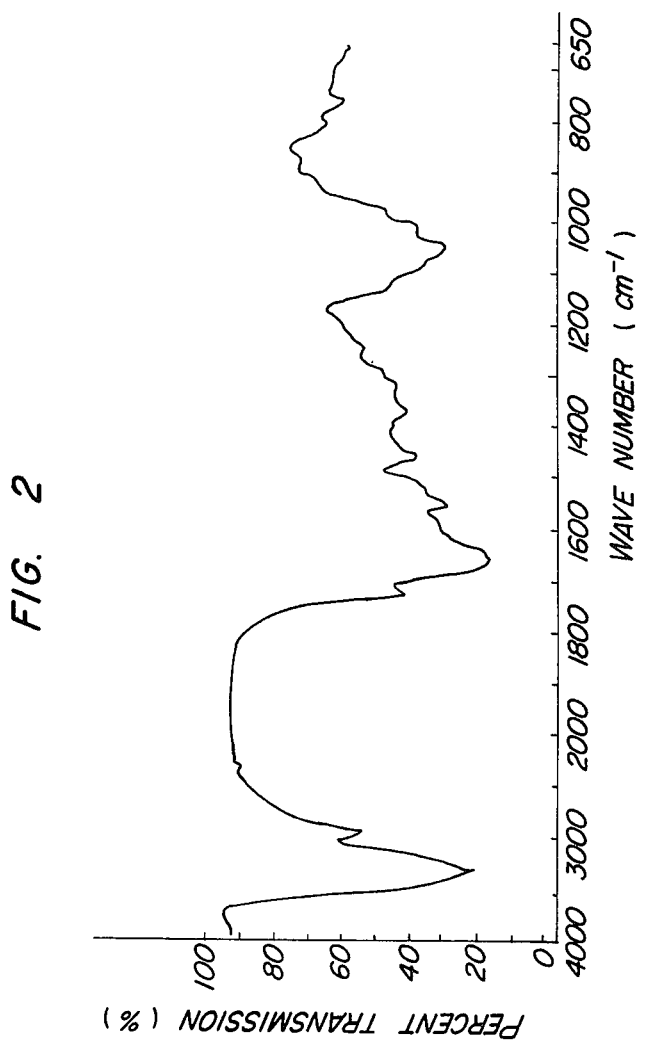

Ultraviolet absorption maxima at 292 m$\mu$ (E 1%, 1 cm = 134) and 244 m$\mu$ (E 1%, 1 cm = 167), similarly to bleomycin $A_2$ (see FIG. 1 of the accompanying drawings). Infrared absorption spectrum is as shown in FIG. 2 of the accompanying drawings, which is the same as that of bleomycin $A_2$, showing absorption maxima at 3600–3100 (3300), 2930, 1720, 1670–1640 (1655), 1585, 1550, 1520, 1458, 1370, 1320, 1245, 1130, 1090, 1050, 1010, 810, 775 (cm$^{-1}$), as measured in potassium bromide tablet.

Values of $R_f$ on chromatograms are as shown in Table 1, which clearly differ from those of bleomycin $A_2$.

Table 1

| Developing solvent system | a | b | c |
|---|---|---|---|
| Demethylbleomycin $A_2$ | 0.80 | 0.78 | 0.71 |
| Bleomycin $A^2$ | 0.41 | 0.44 | 0.85 | a  Silica gel G (trademark for adsorbent for thin-layer chromatography composed of silica gel and gyps manufactured by Merck and Co.) Methanol: 10 %-ammonium acetate = 1:1
b  Silica gel G Methanol: 10 %-ammonium acetate: 10 %-aqueous ammonia = 10:9:1
c  Toyo filter paper No. 51; ascending method 10 %-ammonium chloride.

Demethylbleomycin $A_2$ reacts with Pauly, Ehrlich, Dragendorf, and permanganate reagents in the same manner as that common to Bleomycins; unlike other bleomycins, demethylbleomycin $A_2$ reacts positively with chloroplatinic acid, which is an identification reagent for the grouping $CH_3$—S—.

In order to confirm that the demethylbleomycin $A_2$ obtained according to this invention is a compound having the above-mentioned structure, the present inventors conducted the following examinations.

Firstly, demethylbleomycin $A_2$ (copper-containing hydrochloride) was freed from copper with hydrogen sulfide to obtain demethylbleomycin $A_2$ (copper-free hydrochloride), which was then hydrolyzed by heating with 6N-hydrochloric acid in a sealed tube. The hydrolyzate was subjected to a high voltage paper electrophoresis using a system comprising formic acid : acetic acid : water = 25 : 75 : 900, and then subjected to a two-dimensional paper chromatography (n-propanol : pyridine : acetic acid : water = 15 : 10 : 3 : 12) to obtain the same chromatogram as that obtained in the case of a hydrolyzate of bleomycin $A_2$ except for a color spot of 3-(methylmercapto)propylamine in place of 3-(S,S-dimethylmercapto)propylamine.

Secondly, demethylbleomycin $A_2$ was dissolved in heavy water and NMR (100 MHz) was measured using tetramethylsilane as the external standard. There was observed a signal at $\delta = 2.6$ ppm (singlet) which confirmed the existence of the grouping $CH_3—S—$, while disappearance of the signal was observed at $\delta$ 3.4 ppm assignable to the grouping

which was present in the starting material, i.e., bleomycin $A_2$. Also, no signal was observed either at $\delta = 3.2$ ppm assignable to the grouping

and at $\delta = 3.62$ ppm assignable to the grouping $CH_3SO_2—$.

From the above-said results, it was confirmed that the demethylbleomycin $A_2$ obtained in accordance with this invention is a bleomycin having the above-mentioned structure.

Demethylbleomycin $A_2$ obtained by the process of this invention shows an extremely high antimicrobial activity against *Mycobacterium smegmatis* 607, that is, 2,458 mcg potency/mg as compared with 1000 mcg potency/mg of bleomycin $A_2$. Moreover, as is clear from the following Tables 2 and 3, demethyl bleomycin $A_2$ show the highest index number indicating a large difference between a measure amount showing toxicity and that showing life-prolonging effect as compared with mitomycin C and Bleomycin $A_2$ used as the control medicines. Therefore, it would appear that demethyl bleomycin $A_2$ has the potential of being used far more safely and with greater antitumor effect than bleomycin $A_2$ or mitomycin C, and it can be further said that the therapeutic dosage of demethylbleomycin $A_2$ can be readily decided on the analogy to that of bleomycin complex whose main component is bleomycin $A_2$ and have been already approved as a new antitumor agent in the U.S.A.

Table 2

| Kind of bleomycin | Administered amounts, (mg/kg) | Mean surviving days | | | | | | | |
|---|---|---|---|---|---|---|---|---|---|
| | | 25 | 12.5 | 6.25 | 3.12 | 1.56 | 0.78 | 0.39 | 0.19 | Saline |
| Demethyl bleomycin $A_2$ (Cu-containing hydrochloride) | | 29.0 | 40.5 | 49 | 34.6 | 28.6 | 31.2 | 24.0 | 20.2 | 18.1 |
| Bleomycin $A_2$ (Cu-containing hydrochloride) | | 10.8 | 25 | >28.4 | >36 | >33 | 17.2 | 15.4 | 13.6 | 13.5 |

Mice of ICR/JCL strain (male 5 weeks old, five for one group) are inoculated with Ehrlich ascites carcinoma cells in a dose of 2 millions/mouse.

Bleomycin ranging from 25 mg/kg to 0.19 mg/kg is administered intraperitoneally once a day for 10 days starting from 2 hours after the inoculation, the death is observed every day up to 50 days after inoculation and body weights are measured every 5 days.

Table 3

| Kind of bleomycin | $LD_{50}/ED_{50}$ = Index |
|---|---|
| Demethyl bleomycin $A_2$ (Cu-containing hydrochloride) | 18.0/0.78 = 23 |
| Bleomycin $A_2$ (Cu-containing hydrochloride) | 9.4/0.78 = 12 |
| Mitomycin C (control medicine) | 2.0/0.39 = 5 |

Judgement of the effect $LD_{50}$ is calculated by Behrens-Kärber's method from the group poisoned at high dose levels. A survival percentage at each dose level is obtained by assuming the average number of survival days observed with the control group administered with physilogical saline water to be 100%, and those having survived for such periods as 200% of that of the control or longer are regarded as effective.

The maximum dose level at which they survive for such period as 100 to 200% of the survival days for the control is signified by $ED_{50}$.

With $LD_{50}/ED_{50}$ = Index, it is shown that the higher this value is, the less toxic as well as the more effective the sample tested can be. Moreover, while $LD_{50}$ for an ICR mouse bearing cancer, after daily intraperitoneal administration of bleomycin $A_2$ for 10 days, is 12.5 mg/kg, the corresponding value in the case of demethylbleomycin is 22.5 mg/kg, that is to say, the toxicity of demethylbleomycin $A_2$ is decreased to about half as much. Therefore, demethylbleomycin $A_2$ is a useful substance as a carcinostatic antibiotic.

The invention is illustrated below more concretely with reference to Examples.

EXAMPLE 1

22 Grams of a powder of bleomycin $A_2$ (copper-containing hydrochloride) was heated at 100°C under a reduced pressure (15 mmHg) for 16 hours, and then dissolved in 200 ml of a 0.05 molar aqueous ammonium chloride solution. The resulting solution was passed through a column packed with 800 ml of CM-Sephadex C-25, which had been pretreated with the same solvent as above, to allow the bleomycin component to be adsorbed. Then 690 ml of a 0.1 molar aqueous ammonium chloride solution was passed through the column, and 1780 ml of the eluted blue fraction was collected. The collected elute fraction was then passed through a 500 ml-column packed with an activated carbon for use in chromatography, to allow demethylbleomycin $A_2$ (copper-containing hydrochloride) to be adsorbed thereon. The column was washed with water to remove inorganic salts. Then a 0.02N-HCl-acetone (1 : 1) mixture was passed through the column, and a blue elute solution containing demethylbleomycin $A_2$ (copper-containing hydrochloride) was collected. A basic anion-exchange resin, Dowex 44 (OH-type) (trademark for an ion exchange resin manufactured and sold by Dow Chemical Co.), was added to the collected fraction and pH was adjusted to 6.0. After removing the solvent by distillation and drying, there was obtained 8.91 g of a blue powder of demethylbleomycin $A_2$ (copper-containing hydrochloride) which gradually decomposed at 201° to 212°C.

After having been freed from demethylbleomycin $A_2$ (copper-containing hydrochloride), the CM-Sephadex C-25 still contained undecomposed bleomycin $A_2$. Therefore, the column was again eluted with a 0.1 molar ammonium chloride solution to collect the blue fraction containing bleomycin $A_2$ (copper-containing hydrochloride). The collected fraction is treated in the same manner as in the case of demethylbleomycin $A_2$ (copper-containing hydrochloride) to recover 10.9 g of bleomycin $A_2$ (copper-containing hydrochloride), blue in color.

EXAMPLE 2

To 10 g of a powder of bleomycin $A_2$ (copper-containing hydrochloride), was added 200 ml of toluene, and the mixture was boiled at ordinary pressure under reflux for 6 hours to effect the decomposition. The reaction mixture was filtered to collect a mixture of demethylbleomycin $A_2$ and bleomycin $A_2$. After drying, the mixture was after-treated according to the procedure of Example 1, to obtain 4.1 g of demethylbleomycin $A_2$ (copper-containing hydrochloride) and 3.7 g of undecomposed bleomycin $A_2$ (copper-containing hydrochloride).

EXAMPLE 3

250 Milligrams of a powder of bleomycin $A_2$ (copper-containing hydrochloride) was exposed to dry heat in a vessel at 100°C for 48 hours. The resulting decomposition products were treated according to the procedure of Example 1 to yield 172.5 mg of demethylbleomycin $A_2$ (copper-containing hydrochloride), which was dissolved in 30 ml of methanol. After removal of copper by passing hydrogen sulfide, the methanol solution was concentrated to dryness to obtain 153 mg of white demethylbleomycin $A_2$ (copper-free hydrochloride), which began to decompose gradually at a temperature of 200°C.

EXAMPLE 4

Each 25 mg of a powder of bleomycin $A_2$ (copper-containing hydrochloride) was thermally decomposed under the conditions indicated in Table 4. After-treatment of the decomposed products was carried out according to the procedure of Example 1, to obtain the results as shown in Table 4.

Table 4

|  | Hours | Formed demethyl-bleomycin $A_2$ (Cu-containing hydrochloride), mg | Recovered bleomycin $A_2$ (Cu-containing hydrochloride), mg |
|---|---|---|---|
| Exposed to atmosphere | 3 | 15.5 | 7.7 |
|  | 12 | 16.5 | 6.3 |
|  | 25 | 16.5 | 5.0 |
|  | 48 | 17.2 | 5.0 |
| Under vacuum in sealed tube | 3 | 11.0 | 10.0 |
|  | 12 | 14.5 | 4.9 |
|  | 25 | 14.1 | 5.0 |
|  | 48 | 12.5 | 5.0 |
| Under nitrogen in sealed tube | 3 | 2.0 | 23.7 |
|  | 12 | 13.5 | 4.5 |
|  | 25 | 13.3 | 4.7 |
| Under air in sealed tube | 3 | 10.8 | 11.3 |
|  | 12 | 13.0 | 4.8 |
|  | 25 | 12.2 | 4.5 |
|  | 48 | 12.3 | 4.7 |

EXAMPLE 5

Each 2.0 mg of a powder of bleomycin $A_2$ (copper-containing hydrochloride) was heated at various temperatures as shown in Table 5, under a reduced pressure of 40 mmHg for 3 hours. After-treatment was conducted according to the procedure of Example 1 to obtain the results as shown in Table 5.

Table 5

| Temperature, °C | Formed demethyl-bleomycin $A_2$ (Cu-containing hydrochloride), mg | Recovered bleomycin $A_2$ (Cu-containing hydrochloride), mg |
|---|---|---|
| 60 | 0.08 | 1.89 |
| 80 | 0.26 | 1.69 |
| 100 | 1.04 | 0.64 |
| 120 | 1.25 | 0.45 |
| 140 | 1.23 | 0.21 |

EXAMPLE 6

Each 2.0 mg of a powder of bleomycin $A_2$ (copper-containing hydrochloride) was subjected to anion exchange as shown in Table 6 using a strongly basic anion-exchange resin, and dried. After thermal decomposition of the resulting bleomycin $A_2$ at 100°C under a reduced pressure of 40 mmHg for 3 hours, the decomposed products were after-treated according to the procedure of Example 1 to obtain the results as shown in Table 6.

Table 6

| Anion | Formed demethyl-bleomycin $A_2$ (Cu-containing hydrochloride), mg | Recovered bleomycin $A_2$ (Cu-containing hydrochloride), mg |
|---|---|---|
| $Cl^-$ | 0.82 | 0.82 |
| $Br^-$ | 0.88 | 0.72 |
| $SO_4^{--}$ | 0.44 | 1.14 |
| $H_2NSO_3^-$ | 0.38 | 0.87 |
| 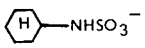 | 0.24 | 1.14 |
| $CH_3COO^-$ | 1.38 | 0.50 |

EXAMPLE 7

2.1 Milligrams of a powder of bleomycin $A_2$ (copper-containing hydrochloride) was suspended in 0.3 ml of o-xylene, thermally decomposed in a sealed tube at 100°C for 3 hours, and then subjected to after-treatment according to the procedure of Example 1, to obtain 0.85 mg of demethylbleomycin $A_2$ (copper-containing hydrochloride) and 0.87 mg of undecomposed bleomycin $A_2$ (copper-containing hydrochloride).

EXAMPLE 8

2.0 Milligrams of a powder of bleomycin $A_2$ (copper-free hydrochloride) was subjected to thermal reaction at 100°C under a reduced pressure of 40 mmHg for 3 hours. After-treatment was carried out according to the procedure of Example 1 to obtain 0.83 mg of demethylbleomycin $A_2$ (copper-free hydrochloride) and 0.42 mg of undecomposed bleomycin $A_2$ (copper-free hydrochloride).

We claim:
1. 3-(Methylmercapto)propylaminobleomycin.
2. 3-(Methylmercapto)propylaminobleomycin having copper contained therein.
3. The copper-containing hydrochloride of 3-(methylmercapto)propylaminobleomycin.
4. Copper free 3-(methylmercapto)propylaminobleomycin.

* * * * *